(12) United States Patent
Mehra et al.

(10) Patent No.: US 12,011,492 B2
(45) Date of Patent: Jun. 18, 2024

(54) WATER-SOLUBLE REFILL DOSE ARTICLE ENCLOSING A CONCENTRATED CLEANSER COMPOSITION AND KITS HAVING SAME

(71) Applicant: HAYDEN PRODUCTS LLC, New York, NY (US)

(72) Inventors: Curan Mehra, New York, NY (US); Konstantinos Lahanas, Paramus, NJ (US)

(73) Assignee: HAYDEN PRODUCTS LLC, New York, NY (US)

( * ) Notice: Subject to any disclaimer, the term of this patent is extended or adjusted under 35 U.S.C. 154(b) by 59 days.

(21) Appl. No.: 17/668,601

(22) Filed: Feb. 10, 2022

(65) Prior Publication Data

US 2022/0265528 A1 Aug. 25, 2022

Related U.S. Application Data

(62) Division of application No. 17/173,401, filed on Feb. 11, 2021, now Pat. No. 11,266,582.

(60) Provisional application No. 62/975,523, filed on Feb. 12, 2020.

(51) Int. Cl.
| | |
|---|---|
| A61K 8/00 | (2006.01) |
| A61K 8/04 | (2006.01) |
| A61K 8/11 | (2006.01) |
| A61K 8/34 | (2006.01) |
| A61K 8/39 | (2006.01) |
| A61K 8/44 | (2006.01) |
| A61K 8/46 | (2006.01) |
| A61K 8/49 | (2006.01) |
| A61K 8/73 | (2006.01) |
| A61K 8/81 | (2006.01) |
| A61Q 1/14 | (2006.01) |
| A61Q 5/02 | (2006.01) |
| A61Q 19/10 | (2006.01) |
| C11D 17/04 | (2006.01) |

(52) U.S. Cl.
CPC ............... *A61K 8/11* (2013.01); *A61K 8/046* (2013.01); *A61K 8/345* (2013.01); *A61K 8/39* (2013.01); *A61K 8/442* (2013.01); *A61K 8/463* (2013.01); *A61K 8/4993* (2013.01); *A61K 8/731* (2013.01); *A61K 8/8152* (2013.01); *A61Q 1/14* (2013.01); *A61Q 5/02* (2013.01); *A61Q 19/10* (2013.01); *C11D 17/04* (2013.01); *C11D 17/041* (2013.01); *A61K 2800/596* (2013.01); *A61K 2800/87* (2013.01)

(58) Field of Classification Search
CPC .................... A61K 8/11; A61K 8/463
See application file for complete search history.

(56) References Cited

U.S. PATENT DOCUMENTS

| | | | |
|---|---|---|---|
| 5,224,601 A | 7/1993 | Gouge et al. | |
| 6,840,408 B1 | 1/2005 | Foster et al. | |
| 6,923,346 B2 | 8/2005 | Foster et al. | |
| 7,013,623 B2 | 3/2006 | Fisher et al. | |
| 7,625,856 B2 | 12/2009 | Burt et al. | |
| 8,105,994 B2 | 1/2012 | Tsaur et al. | |
| 8,113,729 B2 | 2/2012 | Solan | |
| 8,236,747 B2 | 8/2012 | Holzhauer et al. | |
| D702,130 S | 4/2014 | Handy | |
| 8,992,632 B2 | 3/2015 | Holzhauer | |
| 9,237,831 B1 | 1/2016 | Luu et al. | |
| 10,047,327 B2 | 8/2018 | Keuleers et al. | |
| 10,066,195 B2 | 9/2018 | Keuleers et al. | |
| 10,144,908 B2 | 12/2018 | Chandar et al. | |
| 11,607,373 B2 * | 3/2023 | Song | A61K 8/89 |
| 2001/0049345 A1 | 12/2001 | Mumoli | |
| 2003/0077005 A1 | 4/2003 | Fisher et al. | |
| 2003/0161796 A1 | 8/2003 | Bracken et al. | |
| 2004/0115137 A1 | 6/2004 | Verrall et al. | |
| 2004/0229763 A1 | 11/2004 | Hutton et al. | |
| 2005/0205574 A1 | 9/2005 | Lambotte | |
| 2007/0158367 A1 | 7/2007 | Lin | |
| 2008/0051314 A1 | 2/2008 | Wenzel et al. | |
| 2009/0176683 A1 | 7/2009 | Choe et al. | |
| 2009/0221463 A1 * | 9/2009 | Kitko | A61Q 19/10 |
| | | | 510/537 |

(Continued)

FOREIGN PATENT DOCUMENTS

EP 556957 8/1993

OTHER PUBLICATIONS

International Search Report and Written Opinion dated Apr. 5, 2022 in PCT/US21/59945.

(Continued)

*Primary Examiner* — Necholus Ogden, Jr.

(74) *Attorney, Agent, or Firm* — Martin & Ferraro, LLP

(57) ABSTRACT

Water-soluble refill dose articles for forming a cleanser have a water-soluble film defining a first compartment enclosing a first composition and a second compartment enclosing a second composition, which are individual separate articles or are part of an integral article. The first composition has a rheology modifier, a first surfactant, 10% or less by weight water, 20% or less by weight glycol, and the first surfactant does not activate the rheology modifier. The second compartment has an alkaline substance that when mixed with the first composition and water activates the rheology modifier to increase the viscosity of a resulting cleanser and 10% or less by weight water. When the article is diluted in water at a 1:1 to 1:20 ratio, it produces a cleanser having a viscosity within a range of 2000 cps to 50,000 cps.

18 Claims, 1 Drawing Sheet

(56) References Cited

U.S. PATENT DOCUMENTS

| | | |
|---|---|---|
| 2010/0093581 A1 | 4/2010 | Winston et al. |
| 2011/0123608 A1 | 5/2011 | McAllister et al. |
| 2011/0278194 A1 | 11/2011 | Zhu |
| 2011/0288000 A1 | 11/2011 | Crawford et al. |
| 2012/0034314 A1 | 2/2012 | Levison et al. |
| 2013/0277211 A1 | 10/2013 | Joshi et al. |
| 2013/0313154 A1 | 11/2013 | Hernandez et al. |
| 2014/0124535 A1 | 5/2014 | Kelly et al. |
| 2014/0296124 A1 | 10/2014 | Hulskotter et al. |
| 2016/0024447 A1 | 1/2016 | Simonsen et al. |
| 2016/0067155 A1 | 3/2016 | Shimada et al. |
| 2016/0068620 A1 | 3/2016 | Tamareselvy et al. |
| 2016/0075478 A1 | 3/2016 | Godsey et al. |
| 2016/0158776 A1 | 6/2016 | Sternberg et al. |
| 2016/0303043 A1 | 10/2016 | Khoury |
| 2016/0355755 A1 | 12/2016 | Brooker et al. |
| 2017/0183609 A1 | 6/2017 | Hulskotter et al. |
| 2017/0226447 A1 | 8/2017 | Keuleers et al. |
| 2018/0037858 A1 | 2/2018 | Keuleers et al. |
| 2018/0369102 A1* | 12/2018 | Reed ............... A61K 8/463 |
| 2019/0093054 A1 | 3/2019 | Patterson et al. |
| 2019/0239506 A1 | 8/2019 | Macinga et al. |
| 2020/0199497 A1* | 6/2020 | Piorkowski ............ C11D 1/146 |
| 2021/0128415 A1 | 5/2021 | Stern et al. |
| 2021/0169750 A1* | 6/2021 | Maka ............... A61K 8/375 |
| 2021/0230519 A1 | 7/2021 | Watson et al. |
| 2021/0246396 A1 | 8/2021 | Mehra et al. |

OTHER PUBLICATIONS

Https://brandless.com/products/refillable-tub-tile-cleanser-summer-breeze.

International Search Report and Written Opinion dated Apr. 23, 2021 in PCT/US21/17629.

International Search Report and Written Opinion dated Jun. 8, 2021 in PCT/US21/17636.

World's Cleanest Soap—Eco Friendly Refillable Hand Soap + 10 Eco Soap Pods—Mortier Pilon, https://www.mmtumshop.com/collections/mortier-pilon/products/sustainable-hand-soap-glass-bottle-10-orange-soap-refills, first accessed Apr. 12, 2020 (9 pages).

* cited by examiner

WATER-SOLUBLE REFILL DOSE ARTICLE ENCLOSING A CONCENTRATED CLEANSER COMPOSITION AND KITS HAVING SAME

The present application is a continuation of U.S. Ser. No. 17/173,401, filed Feb. 11, 2021; which claims the benefit of U.S. Provisional Application 62/975,523, filed Feb. 12, 2020; which are hereby incorporated by reference in their entirety.

TECHNICAL FIELD

This application relates to a water-soluble refill dose article enclosing a concentrated cleanser composition, more particularly, to a water-soluble refill dose article dissolvable in water to form a liquid cleanser having a viscosity within a range of 2000 cps to 50,000 cps and dispensable from a non-foaming dispenser.

BACKGROUND

Liquid cleansers, such as hand soaps, body wash, shampoos, etc., e.g., those in a filled hand soap dispenser, or a bottle or jug with a large quantity of soap for refilling such dispensers, have a large concentration of water, which contributes to the overall weight of a product. The weight of the product and size of the dispenser or container adds to the manufacturing, packaging costs, and shipping costs. Since clean water is available readily in most of the world and packaging can be re-used, it is wasteful to ship water in the liquid cleansers from one location to another and to use the original packages only once.

Liquid cleanser dispensers are useful in dispensing an appropriate amount of cleanser to a user for proper hygiene, including preventing the transmission of bacteria, viruses, etc. But refilling such dispensers can be difficult because of the heaviness of a bottle or jug of cleanser, which makes it difficult to hold and pour to fill the dispenser. It can also be messy, since dispensers typically have fairly small mouth openings.

Typically, adding water to a concentrate results in a diluted, thinner, i.e., reduced viscosity solution. It is a challenge to develop a concentrated cleanser in a delivery vehicle that upon dilution with water, is easily soluble in water, achieves an acceptable viscosity, and further still foams as expected by the user during a lathering application.

There is a need for a concentrated form of a cleanser that can be dissolved in water to form a suitable cleanser to solve at least the above noted problems and have a desirable viscosity and lather. Here, the solution is a concentrated cleanser stored in a compartment made of water-soluble film, which introduces a multitude of challenges in formulating such a cleanser that will be shelf stable in the compartment.

SUMMARY

By encapsulating cleanser as a concentrated, but diluteable formulation in a water soluble film or pouch, the above problems are overcome. In all aspects, water-soluble refill dose articles for forming a cleanser are disclosed that have a water-soluble film defining a first compartment enclosing a first composition and a second compartment enclosing a second composition. The first compartment and the second compartment are individual separate articles or are part of an integral article. The first composition comprises a rheology modifier and a first surfactant that does not activate the rheology modifier. The first composition has 10% or less by weight water and 20% or less by weight of a glycol. The second composition comprises an alkaline substance that when mixed with the first composition and water activates the rheology modifier to increase the viscosity of a resulting cleanser and has 10% or less by weight water. The individual separate articles or the integral article is added to water at a 1:1 to 1:20 ratio and produces a cleanser having a viscosity within a range of 2000 cps to 50,000 cps.

In all embodiments, the rheology modifier is selected from the group consisting of swellable acrylate polymers, superabsorbent polymers, cellulosic polymers, and combinations thereof and is present as 2% by wt to 10% by wt of the second composition. In one embodiment, the rheology modifier includes a self-wetting polymer, for example acylate/C10-C30 alkyl acrylate crosspolymer.

The first surfactant is present in an amount effective to disperse the rheology modifier in water, which may be as 10% by wt to 99% by wt of the first composition. Additionally, in all aspects, the first composition can includes a plurality of surfactants. In one embodiment, the plurality of surfactants includes a foaming anionic surfactant and one or more of sodium laureth sulfate, sodium lauryl sulfate, sodium lauroyl sarcosinate, polyglyceryl-2-caprate, and disodium cocoglucoside citrate.

In all aspects, the alkaline substance of the second composition can be a surfactant, such as an amido-amine. In another embodiment, the alkaline substance can be a di- or tri-amine; potassium hydroxide, sodium hydroxide, or ammonium hydroxide; an amine having less than 8 carbons, an amido-amine, and combinations thereof. In another embodiment, the alkaline substance is selected from the group consisting of arginine, lysine, histidine, aspartate, glutamate, and combinations thereof. Additionally, the second composition, in all aspects, can include one or more surfactants. The one or more surfactant includes a foaming anionic surfactant. In one embodiment, the one or more surfactants comprise one or more of sodium laureth sulfate, sodium lauryl sulfate, sodium lauroyl sarcosinate, polyglyceryl-2-caprate, and disodium cocoglucoside citrate.

In all aspects, either or both of the first composition and second composition comprise one or more additives selected from the group consisting of a preservative, a coloring agent, a fragrance, an emollient, and an emulsifier.

In another aspect, cleanser kits are disclosed that have a dispenser that discharges a thickened cleanser upon activation by a user and a water-soluble refill dose article. The dispenser has a container defining a preselected cleanser volume. The water-soluble refill dose article has a water-soluble film defining a first compartment enclosing a first composition and a second compartment enclosing a second composition. The first compartment and the second compartment are individual separate articles or are part of an integral article. The first composition comprises a rheology modifier and a first surfactant. The first surfactant does not activate the rheology modifier and the first composition has 10% or less by weight water and 20% or less by weight of a glycol. The second composition has 10% or less by weight water and comprises an alkaline substance that when mixed with the first composition and water activates the rheology modifier to increase the viscosity of a resulting cleanser. The individual separate articles or the integral article is added to water at a 1:1 to 1:20 ratio produces a cleanser having a viscosity within a range of 2000 cps to 50,000 cps.

The dispenser can have a pump removably and sealably engaging a mouth of the container. The pump may be hand-activated or sensor/automatically activated. The kit may have a water-soluble refill dose article disposed inside the dispenser and/or a plurality of the water-soluble refill dose articles packaged to accompany the dispenser. As such, the water-soluble refill dose article is sized and shaped to be smaller than the mouth of the container.

In another aspect, methods for manufacturing a water-soluble refill dose article for forming a gel cleanser are disclosed that include providing a first vessel containing a first composition disclosed herein, providing a second vessel containing a second composition disclosed herein, forming a first compartment defined by a water-soluble film enclosing a first aliquot of the first composition, and forming a second compartment defined by the water soluble film enclosing a second aliquot of the second composition. The first compartment and the second compartment are individual separate articles or are part of an integral article and when such article is added to water at a 1:1 to 1:20 ratio produces a cleanser volume having a viscosity within a range of 2000 cps to 50,000 cps.

DETAILED DESCRIPTION

Figure 1:
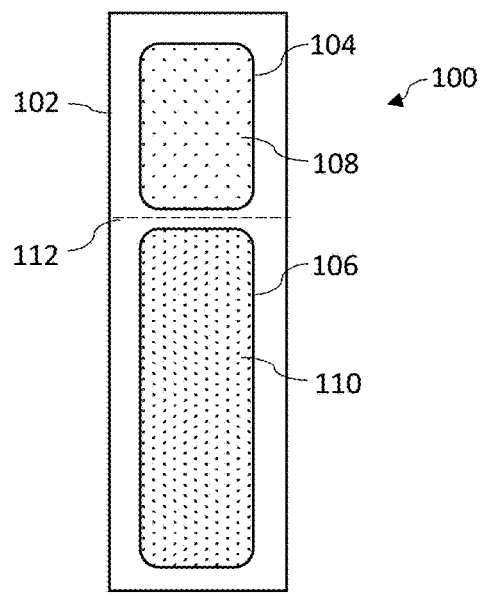
FIG. 1 is a top plan view of a dual compartment water-soluble refill dose article that forms a liquid cleanser upon dilution in water.

The following detailed description will illustrate the general principles of the invention, examples of which are additionally illustrated in the accompanying drawings. In the drawings, like reference numbers indicate identical or functionally similar elements.

Except in the working examples, or where otherwise explicitly indicated, all numbers in this description indicating amounts, parts, percentages, ratios, and proportions of material, physical properties of material, and conditions of reaction are to be understood as modified by the word "about." "About" as used herein means that a value is preferably +/−5% or more preferably +/−2%.

As used herein "refill dose" means an amount of cleanser that is more than a single use volume. Typically, the refill dose defines a cleanser volume that includes a plurality of single use doses and may even form a refill cleanser volume that can fill multiple smaller sized dispensers.

All parts, percentages, ratios, and proportions of material referred to in this description are by weight unless otherwise indicated. It should also be noted that in specifying any range of concentration or amount, any particular upper concentration or amount can be associated with any particular lower concentration or amount.

Figure 2:
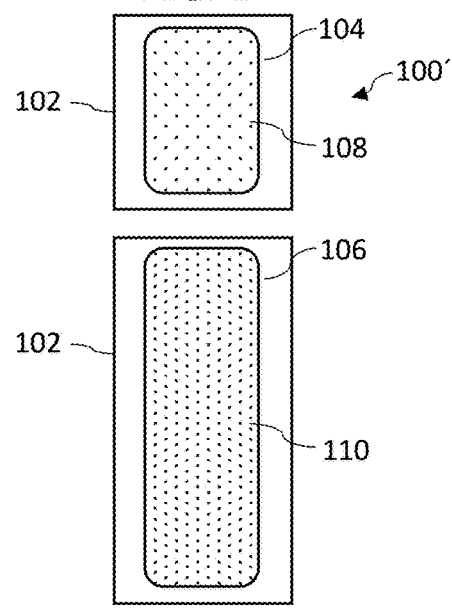
FIG. 2 is a top plan view of duo of water-soluble articles that collectively define a refill dose article that forms a liquid cleanser upon dilution in water.
Figure 3:
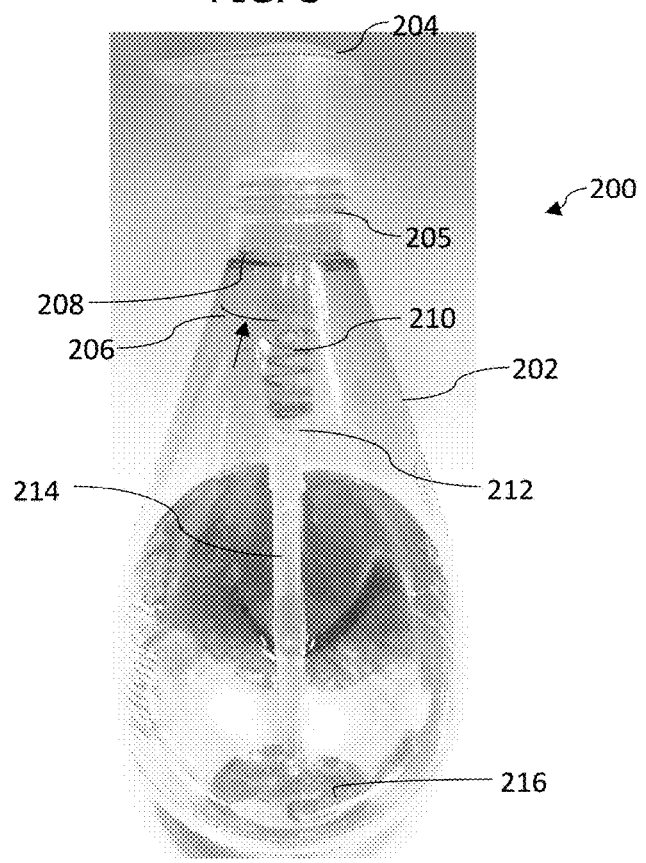
FIG. 3 is a photograph of one embodiment of a cleanser dispenser partially filled with a liquid cleanser.

FIGS. 1 and 2 illustrate an embodiment of a water-soluble refill dose article 100 and 100' that forms a cleanser upon dilution with water. The cleanser may be a hand soap, a body wash, a shampoo, a makeup remover, a facial cleanser, and the like having a viscosity within a range of 2000 cps to 50,000 cps. The water-soluble refill dose article 100 is made of a water-soluble film 102 defining collectively a first compartment 104 enclosing a first composition 108 and a second compartment 106 enclosing a second composition 110. The first composition 108 comprises a rheology modifier and a first surfactant that does not interact with the rheology modifier. The first composition 108 has water and a glycol present and has about 10% or less by weight water and about 20% or less by weight glycol. Glycol as used herein means ethylene glycol, polyethylene glycol, derivatives thereof, and combinations thereof.

The second composition 110 comprises a first alkaline substance that interacts with the rheology modifier to increase the viscosity of a resulting cleanser and has 10% or less by weight water. The second composition may also comprise 20% or less by weight of a glycol. In one embodiment, the second composition is free of glycol. Dashed line 112 is optional, such that rather than being an integral dual compartment article, the first compartment 104 and the second compartment 106 may be separated from one another, if line 112 is a perforation. Alternately, as shown in FIG. 2, the article 100' is a duo of individual, separate water-soluble articles that collectively define the refill dose article. The duo refill dose article 100' when both are placed in a vessel and diluted with water form a cleanser having a viscosity within a range of 2000 cps to 50,000 cps, which may be referred to herein as a gel cleanser. The water-soluble refill dose articles 100 and 100' are combined with water at a 1:1 to 1:20 (refill dose article:water) ratio to produce a cleanser volume that has a viscosity within a range of 2000 cps to 50,000 cps, 3000 cps to 12,000 cps, 4000 cps to 10,000 cps, or more preferably 4000 cps to 6000 cps. The ratio with water is more preferably a 1:5 to 1:15 ratio, and even more preferably a 1:10 ratio. When diluted in water in a dispenser for a cleanser, such as a hand cleanser or body wash, the cleanser volume can be in a range of 50 ml to 18.9 L (5 gal), 100 ml to 7.6 L (2 gal), 100 mL to 1 L, 200 ml to 500 ml.

Methods for manufacturing a water-soluble refill dose article for forming the cleansers described herein include a first vessel that contains the first composition. The first composition has a rheology modifier and a first surfactant. The first surfactant does not interact with the rheology modifier, i.e., activate the thickening, swelling, or particle-to-particle mechanism of the rheology modifier within the solution, and the first composition has 10% or less by weight water and 20% or less by weight glycol. A second vessel is provided that contains the second composition. The second composition has an alkaline substance that when blended with the first composition and water, interacts with the rheology modifier to increase the viscosity of a resulting cleanser and 10% or less by weight water. A first compartment is formed that is defined by a water-soluble film and a first aliquot of the first composition is enclosed therein. A second compartment is formed that is defined by the water soluble film and a second aliquot of the second composition is enclosed therein. The first compartment and the second compartment are individual separate articles or are part of an integral article, which when added to water at a 1:1 to 1:20 ratio produces a cleanser volume having a viscosity within at least one of the ranges disclosed above.

In another embodiment, the first composition and the second composition are prepared, in a manufacturing setting, in separate vessels, each composition comprises less than 10% by weight water such that both compositions are suitable for filling a compartment formed of water soluble film. However, rather than introduce the compositions to compartments formed of a water soluble film, the first and second compositions are introduced simultaneously or sequentially into a vessel of water at a 1:1 to 1:20 ratio to produce a cleanser volume that has a viscosity within a range of 2000 cps to 50,000 cps, 3000 cps to 12,000 cps, 4000 cps to 10,000 cps, or more preferably 4000 cps to 6000 cps. The ratio with water is more preferably a 1:5 to 1:15 ratio, and even more preferably a 1:10 ratio. The manufacturing volume of the vessel may be any commercially reasonable size.

Method for manufacturing a gel cleanser on a commercial scale are disclosed. A first vessel is provided that contains a first composition. The first composition comprises a rheology modifier and a first surfactant. The first surfactant does not interact with the rheology modifier and the first composition has 10% or less by weight water and 20% or less by weight of a glycol. A second vessel is provided that contains a second composition. The second composition has an alkaline substance that interacts with the rheology modifier to increase the viscosity of a resulting cleanser and 10% or less by weight water. A third vessel is provided and into which are introduced a first aliquot of the first composition, a second aliquot of the second composition, and water. The first and second compositions are diluted by the water in a ratio of 1:1 to 1:20 to produce a gel cleanser having a viscosity within at least one of the ranges disclosed above.

Referring again to FIGS. 1 and 2, the water-soluble refill dose articles comprise at least one water-soluble film shaped such that the refill dose article comprises one internal compartment (FIG. 2) or at least two internal compartments (FIG. 1) surrounded by the water-soluble film. In both embodiments, the first compartment comprises a first composition and the second compartment comprises a second composition. The water-soluble film is sealed such that the first and second compositions do not leak out of their respective compartments during storage. However, upon addition of the water-soluble refill dose article 100 or 100' to water, the water-soluble film dissolves and releases the contents of the internal compartments into the water. Each compartment should be understood as meaning a separate closed internal space within the water-soluble article defined by the water-soluble film. Each compartment encapsulates therein, in isolation from one another, its respective composition. The water-soluble article is manufactured such that the water-soluble film completely surrounds each composition and in doing so defines the compartment in which the respective composition resides. Both the first composition and the second composition can be in the liquid phase while stored within their respective compartments of the water-soluble film.

The article may comprise two films. A first film may be shaped to comprise an open compartment into which either of the first or second compositions is added. A second film is then laid over the first film in such an orientation as to close the opening of the compartment. The first and second films are then sealed together along a seal region. Suitable water-soluble films are described in more detail in U.S. Pat. Nos. 7,013,623 and 10,047,327, both of which are incorporated herein in their entirety.

The first and second compartments 104, 106 as illustrated in FIG. 1 are juxtaposed in a side-by side configuration, but in other embodiments may be arranged in a superposed orientation, i.e., one positioned on top of the other, or orientated such that the first compartment at least partially surrounds the second compartment or the first compartment fully surrounds and/or encloses the second compartment. The first and second compartments may be the same size or different sizes. In FIG. 1, the first compartment 104 is smaller than the second compartment 106.

The First Composition

The first composition comprises a rheology modifier selected from the group consisting of swellable acrylate polymers, superabsorbent polymers, cellulosic polymers, and combinations thereof. Such polymers can be cationic, anionic, amphoteric or nonionic and are preferably a self-wetting polymer. They increase the viscosity and stability of liquid formulations. The amount of the rheology modifier in the second composition ranges from 1% by wt to 10% by wt thereof, 2% by wt to 7% by wt thereof, or more preferably 3% by wt to 6% by wt thereof.

Example rheology modifiers include the carbohydrate gums such as cellulose gum, microcrystalline cellulose, cellulose gel, hydroxyethyl cellulose, hydroxypropyl cellulose, hydroxypropyl methylcellulose, sodium carboxymethylcellulose, methyl cellulose, ethyl cellulose, guar gum, gum karaya, gum tragacanth, gum arabic, gum acacia, gum agar, xanthan gum and mixtures thereof; swellable acrylate polymers such as ACULYN® 28 (acrylates/beheneth-25 methacrylate copolymer), ACULYN® 22 (acrylates/steareth-20 methacrylate copolymer) or CARBOPOL® Ultrez 20 (an acrylate/$C_{10}$-$C_{30}$ alkyl acrylate crosspolymer); cationic polymers such as modified polysaccharides including cationic guar available from Solvay under the trade name JAGUAR® C13S, JAGUAR® C14S, JAGUAR® C17, or J JAGUAR® C16; cationic modified cellulose such as UCARE™ Polymer JR 30 or JR 40 from Dow Inc.; synthetic cationic polymer such as MERQUAT® 100, MERQUAT® 280, MERQUAT® 281 and MERQUAT® 550 sold by Lubrizol. Also suitable are high molecular weight polyethylene glycols such as POLYOX® WSR-205 (PEG 14M), POLYOX® WSR-N-60K (PEG 45), and POLYOX® WSR-301 (PEG 90M) from Dow Inc. Example superabsorbent polymers include, but are not limited to, AQUA KEEP™ super absorbent polymer manufactured by Sumitomoseika Chemical Co., sodium polyacrylate, and dehydroxanthan gum.

Typically, the rheology modifier is an acid that is neutralized by a base to form a salt which swells and thickens the composition. In one embodiment, the rheology modifier is a self-wetting polymer such as acrylate/C10-C30 alkyl acrylate crosspolymer and is present as 1% to 10% by weight of the first composition, more preferably 1% to 7% by weight, or 1% to 6% by weight of the first composition. This crosspolymer is sold under the brand Carbopol® by Lubrizol. This polymer is difficult to work with as it collapses easily and can thicken prematurely.

The first composition also has a first surfactant in an amount effective to disperse the rheology modifier in water without interacting with the rheology modifier, i.e., it does not activate thickening of the composition, has 10% or less by weight water, and 20% or less by weight glycol. The first surfactant may be one or more of an anionic surfactant, a nonionic surfactant, and an amphoteric surfactant, but preferably includes at least one foaming surfactant. A foaming surfactant is a surfactant that has as initial foam volume of greater than 10 cm per the Ross-Miles Foam Test (ASTM D1173-53). The first surfactant may be added as a liquid or a solid. In some embodiments, the solid will be dissolved or dispersed in other components of the first composition such that the first composition can be in the liquid phase.

Examples of anionic surfactants suitable for use herein include, but are not limited to, ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, potassium lauryl sulfate, sodium trideceth sulfate, sodium methyl lauroyl taurate, sodium lauroyl isethionate, sodium lauroyl lactylate, sodium laureth sulfosuccinate, sodium lauroyl sulfosuccinate, sodium tridecyl benzene sulfonate, sodium dodecyl benzene sulfonate, sodium lauryl amphoacetate, sodium olefin sulfonate, sodium decyl sulfate, olivoil avenate, disodium coco-glucoside citrate, ammonium ether sulfate, laureth-5 carboxylic acid, potassium olivoyl hydrolyzed oat protein, and mixtures thereof. The anionic surfactant may be, for example, an aliphatic sulfonate, such as a primary $C_8$-$C_{22}$ alkane sulfonate, primary $C_8$-$C_{22}$ alkane disulfonate, $C_8$-$C_{22}$ alkene sulfonate, $C_8$-$C_{22}$ hydroxyalkane sulfonate or alkyl glyceryl ether sulfonate. $C_8$-$C_{22}$ is a range for the length of the carbon chain, including any narrower ranges therein having a minimum and maximum selected from any of $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, and $C_{22}$.

Example nonionic surfactants include, but are not limited to, ethylene maleic anhydride (EMA), sorbitan stearate (e.g., SPAN® 60), sorbitan monooleate (e.g., SPAN® 80), polyethylene glycol sorbitan monooleate (TWEEN® 80), polysorbate (TWEEN® 20), polyvinyl alcohol, ethylene oxide/propylene oxide block copolymers (e.g., PLURONIC® P105), polyoxyethylene (5) nonylphenylether, branched (IGEPAL® CO-520), alcohol ethoxylate, linear alcohol (C9-11) ethoxylate, decyl alcohol ethoxylate, sodium cocoyl glutamate, polyglyceryl-2-caprate, polyglyceryl-3 lactate/laurate, or a mixture thereof. Additionally, polyethylene glycol (PEG), glyceryl, or glycol ethers of fatty alcohols can be used.

Amphoteric surfactants suitable for use herein include, but are not limited to derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one substituent contains an anionic group, e.g., carboxy, sulfonate, sulfate, phosphate, or phosphonate. Illustrative amphoteric surfactants are coco dimethyl carboxymethyl betaine, cocoamidopropyl betaine, cocobetaine, cocamidopropyl hydroxysultaine, oleyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxypropyl betaine, lauryl bis-(2-hydroxypropyl)alpha-carboxyethyl betaine, and mixtures thereof. The sulfobetaines may include stearyl dimethyl sulfopropyl betaine, lauryl dimethyl sulfoethyl betaine, lauryl bis-(2-hydroxyethyl) sulfopropyl betaine and mixtures thereof.

The first surfactant can be any one or more of the surfactants discussed above with respect to the first composition. In one embodiment, the first surfactant includes sodium lauroyl sarcosinate. In another embodiment, the first surfactant comprises a mixture of sodium lauroyl sarcosinate and one or more additional anionic surfactants and a nonionic surfactant, such as a mixture of one or more of sodium laureth sulfate, olivoil avenate, and polysorbate 20.

The Second Composition

The second composition comprises an alkaline substance and has 10% or less by weight water.Alkaline substances include, for example, amino acids, amine salts, amido-amines, di- or tri-amines, short chain amines having less than 8 carbons, for example arginine, hydroxides, such as sodium hydroxide, potassium hydroxide, and ammonium hydroxide, and combinations thereof. The alkaline substance comprises 1% to 100% by weight of the second composition.

Suitable amino acids include, but are not limited to arginine, lysine, histidine, aspartate, and glutamate.

Suitable amine salts include, but are not limited to, ethoxylated tallow amine, cocoalkylamine, and oleylamine.

Suitable amido-amines include, but are not limited to, stearamido-propyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylmine, behenamidoethyldiethylamine, behenamidoethyldimethylamine, arachidamidopropyldimethylamine, arachidamidopropyldiethylamine, arachid-amidoethyldiethylamine, arachidamidoethyldimethylamine, and mixtures thereof. Commercially available amido-amines useful herein include: stearamidopropyldimethylamine with tradenames LEXAMINE S-13 available from Inolex (Philadelphia Pa., USA), behenamidopropyldimethylamine with a tradename INCROMINE BB available from Croda (North Humberside, England), and various amido-amines, preferably tertiary amido-amines, with tradenames SCHERCODINE series available from Lubrizol (Ohio, USA).

Suitable di- or tri-amines include, but are not limited thereto, triethanolamine and N,N,N',N'-tetrakis(2-hydroxypropyl)ethylenediamine, solutions of short chain amines.

The second composition can also comprise one or more additional surfactants, preferably liquid surfactants, such as those discussed above with respect to the first composition. When present, the one or more additional surfactants are present as 5% by wt to 70% by wt of the first composition, as 10% by wt to 60% by wt, more preferably 20% by wt to 60% by wt. The surfactants can be anionic, nonionic, amphoteric, and mixtures thereof.

In one embodiment, the one or more additional surfactants include sodium laureth sulfate. In another embodiment, the one or more additional surfactants include sodium laureth sulfate and a second anionic surfactant. The second anionic surfactant is preferably selected from sodium lauroyl sarcosinate, disodium coco-glucoside citrate, and olivoil avenate. In yet another embodiment, the one or more additional surfactants includes sodium laureth sulfate and a nonionic surfactant. Preferably, the nonionic surfactant is polysorbate 20.

Each surfactant may be present as a liquid or a solid, understanding that any solids will ultimately be dissolved in water. In one embodiment, a solid surfactant is dissolved or dispersed in another component of the first composition or the second composition, such that the respective composition is in the liquid phase. Some examples of solid surfactants include, but are not limited to PEG-7 glyceryl cocoate, sodium lauroyl sarcosinate, and sodium $C_{14}$-$C_{16}$ alpha olefin sulfonate.

Preservative

Either or both of the first composition and second composition comprise a preservative in a total effective amount for the preselected cleanser volume. The "total effective amount" is the total amount of preservative in the one or more compartments that upon dilution with water to the preselected cleanser volume is present in a preservative effective amount to give the preselected cleanser volume a shelf-life suitable to industry standards. The total effective amount of the preservative is in a range of 1% by weight to 25% by weight and the amount of preservative in the preselected cleanser volume is in a range of 0.1% by weight to 2% by weight.

The preservatives protect the resulting gel cleanser against the growth of potentially harmful microorganisms. Suitable preservatives include, but are not limited to, alkyl esters of para-hydroxybenzoic acid, hydantoin derivatives, propionate salts, and a variety of quaternary ammonium compounds. Among the preservatives of particular interest are phenoxyethanol, methyl paraben, propyl paraben, imidazolidinyl urea, sodium dehydroacetate and benzyl alcohol.
Additives Either or both of the first composition and the second composition comprise one or more additives. The additives may be selected from the group consisting of coloring agents, fragrances, skin and/or hair benefit agents, UV absorbers, and emulsifiers.

The term skin and/or hair benefit agent, collectively "benefit agents" is typically a substance which softens or improves the elasticity, appearance, and youthfulness of the skin (stratum corneum) by either increasing its water content, adding, or replacing lipids and other skin nutrients, or both, and keeps it soft by retarding the decrease of its water content. For hair, the benefit agent is typically a substance that conditions, strengthens, repairs, smooths, reduces static, imparts style-retention properties, color, or provides another benefit to the hair. Included among the suitable skin benefit agents are emollients, including, for example, hydrophobic emollients, hydrophilic emollients, or blends thereof.

Useful benefit agents include the following: (a) silicone oils and modifications thereof such as linear and cyclic polydimethylsiloxanes; amino, alkyl, alkylaryl, and aryl silicone oils; (b) fats and oils including natural fats and oils such as jojoba, soybean, sunflower, rice bran, avocado, almond, olive, sesame, persic, castor, coconut, and mink oils; cacao fat; beef tallow and lard; hardened oils obtained by hydrogenating the aforementioned oils; and synthetic mono, di and triglycerides such as myristic acid glyceride and 2-ethylhexanoic acid glyceride; (c) waxes such as carnauba, spermaceti, beeswax, lanolin, and derivatives thereof; (d) hydrophobic and hydrophilic plant extracts; (e) hydrocarbons such as liquid paraffin, petrolatum, microcrystalline wax, ceresin, squalene, pristan and mineral oil; (f) higher fatty acids such as lauric, myristic, palmitic, stearic, behenic, oleic, linoleic, linolenic, lanolic, isostearic, arachidonic and poly unsaturated fatty acids (PUFA); (g) higher alcohols such as lauryl, cetyl, stearyl, oleyl, behenyl, cholesterol and 2-hexydecanol alcohol; (h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol monolaurate, glycerol distearate, glycerol tristearate, alkyl lactate, alkyl citrate and alkyl tartrate; (i) essential oils and extracts thereof such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, sesame, ginger, basil, juniper, lemon grass, rosemary, rosewood, avocado, grape, grapeseed, myrrh, cucumber, watercress, calendula, elder flower, geranium, linden blossom, amaranth, seaweed, ginko, ginseng, carrot, guarana, tea tree, jojoba, comfrey, oatmeal, cocoa, neroli, vanilla, green tea, penny royal, aloe vera, shea oil, menthol, cineole, eugenol, citral, citronelle, borneol, linalool, geraniol, evening primrose, camphor, thymol, spirantol, penene, limonene and terpenoid oils; (j) polyhydric alcohols, for example, glycerine, sorbitol, propylene glycol, and the like; and polyols such as the polyethylene glycols, examples of which are: Polyox WSR-205 PEG 14M, Polyox WSR-N-60K PEG 45M, or Polyox WSR-N-750, and PEG 7M; (k) lipids such as cholesterol, ceramides, sucrose esters and pseudo-ceramides as described in European Patent Specification No. 556,957; (l) vitamins, minerals, and skin nutrients such as milk, vitamins A, E, and K; vitamin alkyl esters, including vitamin C alkyl esters; magnesium, calcium, copper, zinc and other metallic components; (m) sunscreens such as octyl methoxyl cinnamate (Parsol MCX) and butyl methoxy benzoylmethane (Parsol 1789); (n) phospholipids; (o) anti-aging compounds such as alpha-hydroxy acids and beta-hydroxy acids; and (p) quaternary ammonium compounds such as cetyl trimethyl ammonium bromide, myristyl trimethyl ammonium bromide, stearyl dimethyl benzyl ammonium chloride, lauryl/myristyl trimethyl ammonium methosulfate, stearyl octyldimonium methosulfate, dihydrogenated palmoylethyl hydroxyethylmonium methosulfate, isostearyl benzylimidonium chloride, cocoyl benzyl hydroxyethyl imidazolinium chloride, cocoyl hydroxyethylimidazolinium.

Example hair benefit agents are found in US 2003/0161796, and example skin and hair benefit agents are found in U.S. Pat. No. 8,105,994. The examples from both patent references are incorporated herein by reference.

Benefit agents commonly account for up to 30% weight of the preselected cleanser volume, with levels of from 0% to 25% weight, more particularly from 0% to 20% weight, being typical of the levels at which those skin benefit agents generally known as "emollients" are employed in many of the subject formulations. Preferred skin benefit agents include fatty acids, hydrocarbons, polyhydric alcohols, polyols and mixtures thereof, with emollients that include at least one $C_{12}$ to $C_{18}$ fatty acid, petrolatum, glycerol, sorbitol and/or propylene glycol.

Additional optional ingredients which may be present in the cleansing formulations are, for example: sequestering and chelating agents such as tetrasodium ethylenediaminetetraacetate (EDTA), ethane hydroxyl diphosphonate (EHDP), and etidronic acid, aka 1-hydroxyethylidene diphosphonic acid (HEDP); opacifiers and pearlizers such as zinc stearate, magnesium stearate, $TiO_2$, ethylene glycol monostearate (EGMS), ethylene glycol distearate (EGDS) or Lytron 621 (Styrene/Acrylate copolymer) and the like; pH adjusters; antioxidants, for example, butylated hydroxytoluene (BHT) and the like; stabilizers such as benzotriazolyl dodecyl p-cresol (a broadband UV absorber for stabilization of transparent packaged products); and other ingredients such as are conventionally used in liquid cleanser formulations. The total amount of such additional optional ingredients is typically from 0% to 10% by weight, more particularly from 0.1% to 5% by weight, based on the total weight of the cleanser volume.
Kit The water-soluble refill dose articles 100 and 100' both comprise a concentrated cleanser formulation that when placed in a vessel, such as dispenser 200 of FIG. 2, and combined with water will create a thickened cleanser.

Cleanser kits include a dispenser that discharges a cleanser upon activation by a user and a water-soluble refill dose article as described above. Referring to FIG. 2, a dispenser 200 has a container 202 defining a preselected cleanser volume, as noted by the fill line 206, and a pump 204 that is removably and sealably engaging a mouth 208 of the container, for example, by a threaded neck 205. The pump 204 includes a spring 210 seated inside a larger diameter tube 212 and a smaller diameter tube 214 inserted in the larger diameter tube and extending to an interior bottom 216 of the container 202. The water-soluble refill dose article 100 is dissolvable in water to form a gel cleanser having the preselected cleanser volume of the container and having a viscosity within the ranges disclosed above. And, after water is added to the container 202 to the fill line 206, the water-soluble refill dose article dissolves to form a gel cleanser within the dispenser 200. Gentle swishing by the user will aid in the mixing and dissolving of the water-soluble refill dose article.

The pump 204 of the dispenser is a hand-actuatable pump, but may include a sensor for automatic dispensing of the gel cleanser. In another embodiment, the dispense can be a squeeze bottle. The fill line 206 identifies a preselected cleanser volume for the container 202. The size and shape of the dispenser can be selected to fit the user's needs.

The kit may have one water-soluble refill dose article disposed inside the container of the dispenser, without water present, at the point of sale. The kit may include one or more additional water-soluble refill dose articles accompanying the dispenser. Alternately, the kit may include an empty dispenser and a packet containing a plurality of water-soluble refill dose articles.

The water-soluble refill dose article is sized and shaped to be smaller than the mouth 208 of the container 202. In one embodiment, the water-soluble refill dose article is generally cylindrically shaped and has a diameter less than 5 cm, more preferably less than 3 cm.

In the composition of Table 1, the percent by weight of water is 10% or less, i.e., the sum of the weight percent of water (A), water (B), water (C), and water (D) equals at most 10% wt/wt for the first composition and the sum of the weight percent of water (E), water (F), and water (G) equals at most 10% wt/wt for the second composition. A minimum value of 0% is used to demonstrate that the particular substance is optional. However, when such optional substances are present, the minimum may be 0.1% by weight or 1% by weight, or 2% by weight, or 3% by weight, or 4% by weight, or 5% by weight.

For the first composition of Examples 1-3 above, at room temperature (typically about 25° C.), in a main vessel the phenoxyethanol and Shebu oil were mixed until uniform. Then, the surfactant blend was added with mixing. Next, the other surfactants, i.e., the sodium laureth sulfate and the olivoil avenate surfactant, and the Carbopol® Ultrez 20 polymer were added to the main vessel with mixing. In a separate vessel any fragrance(s) were mixed with the polysorbate 20. Then, the polysorbate 20 mixture was added to the main vessel with mixing. Lastly, any colorants were added with mixing until a uniform solution was formed.

For the second composition of Examples 1-3 above, at room temperature (typically about 25° C.), in a main vessel the amido-amine was mixed with the surfactant(s) and preservative until uniformly blended.

Working Examples

| First Composition for First Compartment | Minimum | Example 1 (% wt/wt) | Example 2 (% wt/wt) | Example 3 (% wt/wt) | Maximum |
|---|---|---|---|---|---|
| Surfactant Blend | (1%) | — | — | — | (70%) |
| 'propylene glycol | 0.25% | 9.5% | 9.8% | 9.5% | 17.5% |
| 'disodium coco-glucoside citrate | 0.25% | 9.5% | 9.8% | 9.5% | 17.5% |
| 'sodium lauroyl sarcosinate | 0.2% | 7.6% | 7.8% | 7.6% | 14% |
| 'polyglyceryl-2-Caprate | 0.25% | 9.5% | 9.8% | 9.5% | 17.5% |
| 'water (A) | 0.05% | 1.9% | 1.9% | 1.9% | 3.5% |
| CARBOPOL ® Ultrez 20 | 1% | 6.0% | 4.2% | 6.0% | 10% |
| sodium laureth sulfate (70%) | 0% | 8.4% | 17.5% | 8.4% | 33.3% |
| 'water (B) | | 3.6% | 7.5% | 3.6% | 10% |
| Olivoil Avenate Surfactant (25-35%) | 0% | 0.035% | 0.035% | 0.035% | 3.5% |
| 'water (C) | | 0.065% | 0.065% | 0.065% | 6.5% |
| Shebu Oil | 0% | 0.4% | 0.3% | 0.4% | 10% |
| Phenoxyethanol | 0.1% | 16.7% | 12.5% | 16.7% | 20% |
| polysorbate 20 | 0% | 17.4% | 12.2% | 17.4% | 48.5 |
| 'water (D) | | 0.5% | 0.3% | 0.5% | 1.5% |
| Fragrance | 0% | 8.9% | 6.3% | 8.9% | 30% |
| | | 100.0% | 100.0% | 100.0% | |

| Second Composition for Second Compartment | Minimum | Example 1 (% wt/wt) | Example 2 (% wt/wt) | Example 3 (% wt/wt) | Maximum |
|---|---|---|---|---|---|
| SCHERCODINE ™ C amido-amine | 1% | 28.8% | 100.0% | 43.3% | 100% |
| sodium laureth sulfate (70%) | 0% | 26.9% | — | 20.2% | 33.3% |
| 'water (E) | 0% | 8.7% | — | 8.6% | 10% |
| Phenoxyethanol | 0% | 1.9% | — | 1.2% | 20% |
| polysorbate 20 | 0% | 32.7% | — | — | 48.5% |
| ' water (F) | 0% | 1.0% | — | — | 1.5% |
| Surfactant Blend | 0% | — | — | | 70% |
| 'propylene glycol | 0% | — | — | 6.7% | 17.5% |
| 'disodium coco-glucoside citrate | 0% | — | — | 6.7% | 17.5% |
| 'sodium lauroyl sarcosinate | 0% | — | — | 5.3% | 14% |
| 'polyglyceryl-2-Caprate | 0% | — | — | 6.7% | 17.5% |
| 'water (G) | 0% | — | — | 1.3% | 3.5% |
| | | 100.0% | | 100.0% | |

In one embodiment, the first composition has a larger mass in grams and a larger volume than the second composition. The first compartment has a chamber size ratio to that of the second compartment of 1.6:1 to 8:1.

If desired, an additional compartment or a subchamber formed of water-soluble film can be included to enclose any desirable single or multi-component formulation to provide a preselected attribute to the concentrated cleanser once diluted with water or to move any component(s) from one of the first and second compartments discussed herein to its own compartment or subchamber.

By encapsulating the cleanser as a concentrated, but diluteable formulation in a water-soluble film or pouches, the packaging weight of the product and its size is reduced for reduced shipping and packaging costs. The product can be shipped to any location, placed into a dispenser container, and, upon filling the dispenser with water, dissolved in water to form a gel cleanser. Further, the dual compartment water-soluble article separates a rheology modifier (thickener) from a surfactant that interact with one another to thicken or swell upon dilution in water to create a gel cleanser having a desired viscosity.

It should be noted that the embodiments are not limited in their application or use to the details of construction and arrangement of parts and steps illustrated in the drawings and description. Features of the illustrative embodiments, constructions, and variants may be implemented or incorporated in other embodiments, constructions, variants, and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

Having described the invention in detail and by reference to preferred embodiments thereof, it will be apparent that modifications and variations are possible without departing from the scope of the invention which is defined in the appended claims.

What is claimed is:

1. A water-soluble refill dose article for forming a cleanser comprising:
   a water-soluble film defining a first closed internal space in which a first composition is encapsulated as a liquid phase and a second closed internal space in which a second composition is encapsulated as a liquid phase;
   the first composition comprises:
      a rheology modifier comprising an acylate/C10-C30 alkyl acrylate crosspolymer;
      a first surfactant that does not activate the rheology modifier;
      about 10% or less by weight water; and
      about 20% or less by weight glycol;
   the second composition comprises:
      an alkaline substance that when mixed with the first composition and water activates the rheology modifier to increase the viscosity of a resulting cleanser to a viscosity within a range of 2000 cps to 50,000 cps; and
      about 10% or less by weight water; and
   wherein the water-soluble refill dose article has an article to water ratio in a range of 1 article to 1 to 20 water by volume dilution to produce a preselected cleanser volume of a resulting cleanser that is dispensable through a pump as a liquid gel cleanser.

2. The article of claim 1, wherein the rheology modifier further comprises a superabsorbent polymer, a cellulosic polymer, or a combination thereof.

3. The article of claim 2, wherein the first surfactant is present in an amount effective to disperse the rheology modifier in the preselected cleanser volume.

4. The article of claim 2, wherein the first surfactant is present as 10% by wt to 99% by wt of the first composition.

5. The article of claim 2, wherein the first surfactant comprises one or more of sodium laureth sulfate, sodium lauryl sulfate, sodium lauroyl sarcosinate, polyglyceryl-2-caprate, and disodium cocoglucoside citrate.

6. The article of claim 1, wherein the first surfactant is a foaming anionic surfactant.

7. The article of claim 1, wherein the rheology modifier is present as 2% by wt to 10% by wt of the first composition.

8. The article of claim 1, wherein the alkaline substance is a surfactant.

9. The article of claim 8, wherein the alkaline substance is an am ido amine or a di- or tri-amine, potassium hydroxide, sodium hydroxide, ammonium hydroxide, or an amine having less than 8 carbons.

10. The article of claim 1, wherein the second composition comprises one or more surfactants.

11. The article of claim 10, wherein the one or more surfactants comprise one or more of sodium laureth sulfate, sodium lauryl sulfate, sodium lauroyl sarcosinate, polyglyceryl-2-caprate, and disodium cocoglucoside citrate.

12. The article of claim 11, wherein the one or more surfactants comprise a foaming anionic surfactant.

13. The article of claim 1, wherein either or both of the first composition and second composition comprise polysorbate 20.

14. The article of claim 1, wherein either or both of the first composition and the second composition comprise a preservative in an effective amount for the resulting cleanser volume.

15. The article of claim 1, further comprising one or more additives selected from the group consisting of a coloring agent, a fragrance, an emollient, and an emulsifier.

16. The article of claim 1, wherein the first closed internal space and the second closed internal space are individual separate articles or are part of an integral article.

17. The article of claim 1, wherein the cleanser is a topical cleanser for skin and/or hair.

18. A method for manufacturing a water-soluble refill dose article for forming a cleanser comprising:
   providing a first vessel containing a first composition in a liquid phase, the first composition comprising a rheology modifier and a first surfactant; wherein the first surfactant does not activate the rheology modifier, the rheology modifier comprises an acylate/C10-C30 alkyl acrylate crosspolymer, and the first composition has 10% or less by weight water and 20% or less by weight glycol;
   providing a second vessel containing a second composition in a liquid phase, the second composition comprises an alkaline substance that when mixed with the first composition and water activates the rheology modifier to increase the viscosity of a resulting cleanser; wherein the second composition has 10% or less by weight water; and
   forming a first compartment defined by a water-soluble film enclosing a first aliquot of the first composition;
   forming a second compartment defined by the water soluble film enclosing a second aliquot of the second composition;

wherein the first compartment and the second compartment are individual separate articles or are part of an integral article;

wherein adding the individual separate articles or the integral article to water at a 1:1 to 1:20 ratio produces a cleanser volume having a viscosity within a range of 2000 cps to 50,000 cps for a resulting cleanser that is dispensable through a pump as a liquid gel cleanser.

* * * * *